(12) United States Patent
Shukla et al.

(10) Patent No.: US 7,544,828 B2
(45) Date of Patent: Jun. 9, 2009

(54) PROCESS FOR PREPARATION OF BICALUTAMIDE

(75) Inventors: Anil Kumar Shukla, Sahibabad (IN); Golak Chandra Maikap, Sahibabad (IN); Shiv Kumar Agarwal, Sahibabad (IN)

(73) Assignee: Dabur Pharma Limited, Kolkata (IN)

( * ) Notice: Subject to any disclaimer, the term of this patent is extended or adjusted under 35 U.S.C. 154(b) by 279 days.

(21) Appl. No.: 11/582,716

(22) Filed: Oct. 17, 2006

(65) Prior Publication Data

US 2007/0149800 A1      Jun. 28, 2007

(30) Foreign Application Priority Data

Dec. 27, 2005    (IN) .................................. 1187/2005

(51) Int. Cl.
   *C07D 255/00*     (2006.01)
(52) U.S. Cl. ....................................... 558/411; 558/303
(58) Field of Classification Search ................. 558/303, 558/411

See application file for complete search history.

(56) References Cited

U.S. PATENT DOCUMENTS

| 4,636,505 | A | 1/1987 | Tucker |
| 6,740,770 | B2 | 5/2004 | Shintaku et al. |
| 2004/0013303 | A1 | 1/2004 | Lienhart et al. |
| 2004/0063782 | A1 | 4/2004 | Westheim |

FOREIGN PATENT DOCUMENTS

| WO | 01/00608 A1 | 1/2001 |
| WO | 02/24638 A1 | 3/2002 |
| WO | 2004/074350 A2 | 9/2004 |
| WO | 2005/037777 A1 | 4/2005 |

OTHER PUBLICATIONS

"Oxidizing agent," http://en.wikipedia.org/wiki/Oxidizing_agent, Retrieved online via Internet, Sep. 22, 2008.*

Tucker et al. "Nonsteroidal antiandrogens. Synthesis and structure-activity relationships of 3-substituted derivatives of 2-hydroxypropionanilides" vol. 31, No. 5 p. 954-959 (1988).

* cited by examiner

Primary Examiner—Kamal A Saeed
Assistant Examiner—Samantha L Shterengarts
(74) Attorney, Agent, or Firm—Merchant & Gould P.C.

(57) ABSTRACT

A process for preparation of Bicalutamide of formula (I),

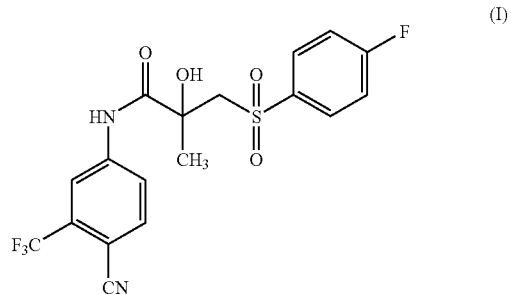

comprising oxidation of compound of formula (II),

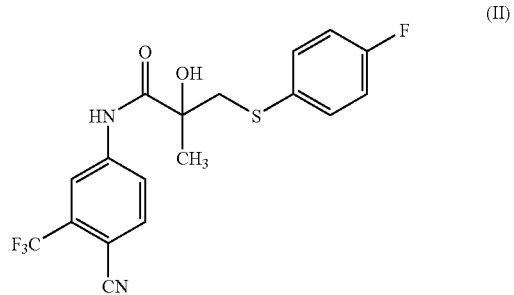

with potassium permanganate in presence of water or a mixture of water and water miscible solvent and isolating Bicalutamide of formula (I) thereof.

23 Claims, 4 Drawing Sheets

X-ray diffraction pattern of Bicalutamide (I) obtained as per the method of the present invention.

DSC thermo gram of Bicalutamide (I) obtained as per the method of the present invention.

PROCESS FOR PREPARATION OF BICALUTAMIDE

FIELD OF THE INVENTION

The present invention relates to an improved process for preparation of Bicalutamide, which is simple, convenient, safe and cost effective.

BACKGROUND OF THE INVENTION

Bicalutamide, which is chemically known as N-[4-cyano-3-(trifluoromethyl) phenyl]-3-[(4-fluorophenyl) sulfonyl]-2-hydroxy-2-methyl propanamide and represented by formula (I),

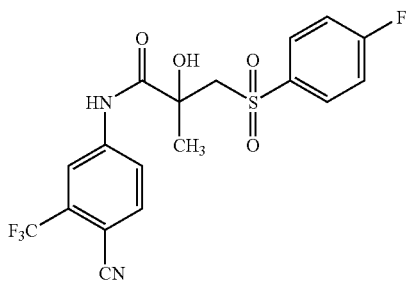

(I)

is a non-steroidal anti-androgen used in combination therapy with a Luteinizing Hormone Releasing Hormone (LHRH) analogue for treatment of advanced prostate cancer.

The first synthesis of Bicalutamide was disclosed by Tucker in U.S. Pat. No. 4,636,505, the key step essentially comprising oxidation of N-[4-cyano-3-(trifluoromethyl) phenyl]-3-[(4-fluorophenyl) thio]-2-hydroxy-2-methyl propanamide of formula (II),

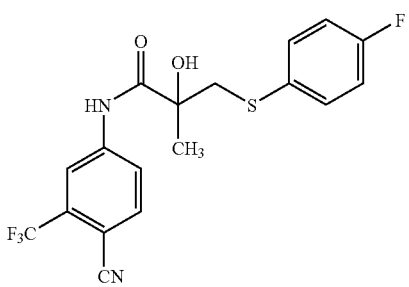

(II)

to give Bicalutamide of formula (I). The sulfide compound is in turn prepared through reaction of 4-cyano-3-trifluoromethyl N-(2,3-epoxy-2methyl propionyl) aniline of formula (III)

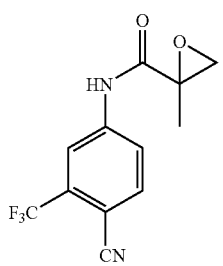

(III)

with p-fluorothio phenol.

The synthesis of Bicalutamide as disclosed in U.S. Pat. No. 4,636,505 is summarized in Scheme-I Scheme-I Synthesis of Bicalutamide as disclosed in U.S. Pat. No. 4,636,505

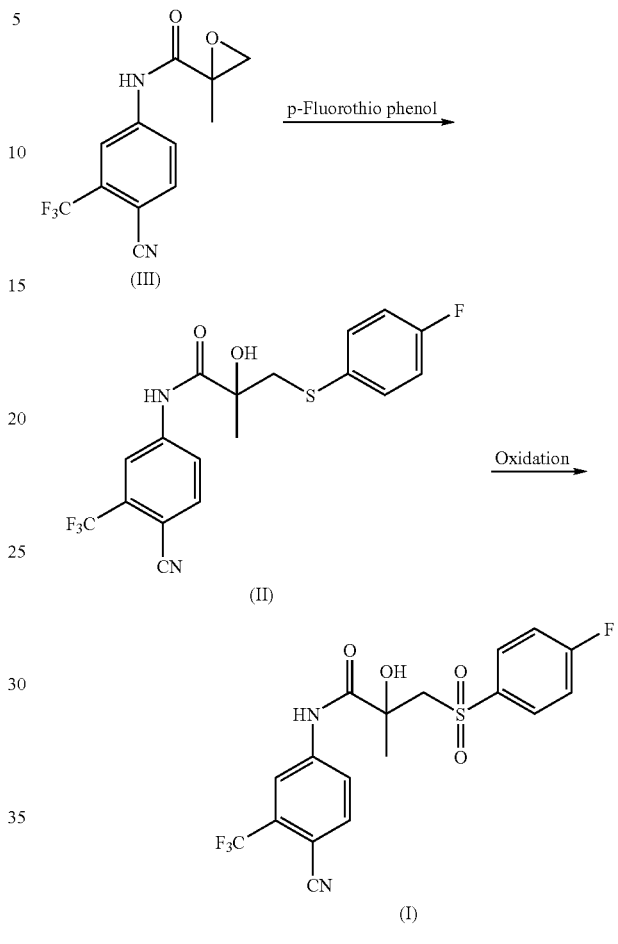

U.S. Pat. No. 4,636,505 mentions that the oxidizing agent and conditions used will determine whether a sulfinyl (S→O) or a sulfonyl (O═S═O) compound is obtained. Thus, oxidation with sodium metaperiodate in methanol solution at or below laboratory temperature was considered to convert a thio compound into the corresponding sulfinyl compound; and oxidation with a peroxy acid, for example m-chloroperbenzoic acid, in methylene chloride solution at or above laboratory temperature was considered to convert a thio compound into the corresponding sulfonyl compound. From the above as well as the description given in Example 6 of U.S. Pat. No. 4,636,505 it would be abundantly evident that the most preferred oxidizing agent is a peroxy acid, especially m-chloroperbenzoic acid.

A similar synthesis of Bicalutamide comprising oxidation of the sulfide (II) with m-chloroperbenzoic acid is disclosed by Tucker et al in *Journal of Medicinal Chemistry*, 1988, Vol. 31, No. 5 page 954-959.

Many variants/improvements of Bicalutamide synthesis have been subsequently reported, all of which in particular relate to certain improvements in the step of oxidation of sulfide (II) to Bicalutamide. These are:

i). Soros et al in WO 01/00608 A1, while stating that the method disclosed in U.S. Pat. No. 4,636,505 and *Journal of Medicinal Chemistry*, 1988, Vol. 31, No. 5 page 954-959 is not industrially and environmentally safe provide an improved method comprising oxidation of the sulfide (II)
a) with an inorganic peroxy salt in a mixture of water and a solvent miscible or immiscible with water, in the latter case in the presence of a phase transfer catalyst, or
b) with aqueous hydrogen peroxide in presence of a $C_1$-$C_4$ aliphatic carboxylic acid, or under aqueous basic conditions, in presence of an organic solvent miscible with water, or in an organic solvent immiscible with water in the presence of a phase transfer catalyst and a salt of a metal belonging to the vanadium or chromium group.

ii). Chen, Bang-Chi et al in WO 02/24638 A1 also disclose oxidation of sulfide (II) using conventional oxidizing agents known in the art, specifically a peroxy acid, such as peracetic acid, trifluoroperacetic acid, 3-chloroperbenzoic acid, and the like; dioxiranes such as dimethyldioxirane, methyltrifluoromethyldioxirane, and the like; hydrogen peroxide; sodium periodate; N-methylmorpholine; N-oxide and Oxone, with peroxy acids in particular trifluoroacetic acid being more preferable. The specification further states that trifluoroperacetic acid is preferably formed in situ from hydrogen peroxide and trifluoroacetic anhydride. Typically the oxidation is carried out by treating a solution of sulfide (II) in dichloromethane with 30% aqueous hydrogen peroxide solution and cooling the mixture to −55° C., followed by addition of trifluoroacetic anhydride and allowing the oxidation to proceed at a temperature of between −15° C. to 0° C.

iii). Tetsuya et al in U.S. Pat. No. 6,740,770 have criticized the method disclosed by Tucker et al in *Journal of Medicinal Chemistry,* 1988, Vol. 31, No. 5 page 954-959 as well as U.S. Pat. No. 4,636,505 in that they utilize dichloromethane as a solvent in the oxidation step, which is harmful, potentially carcinogenic, expensive and creates a burden in waste treatment. U.S. Pat. No. 6,740,770 further criticizes the method disclosed by Tucker et al in *Journal of Medicinal Chemistry,* 1988, Vol. 31, No. 5 page 954-959 as using m-chloroperbenzoic acid as an oxidizing agent, which is not only highly explosive but also expensive and possess an economic problem.

Furthermore, U.S. Pat. No. 6,740,770 criticizes the methods disclosed by WO 01/00608 A1 and WO 02/24638 A1 as also not industrially and environmentally benign as well as not safe and expensive in that the said methods are found to utilize again dichloromethane in one of the steps, utilize cryogenic temperature of −55° C., utilize expensive trifluoroacetic anhydride as a reactant.

Accordingly, U.S. Pat. No. 6,740,770 provides an alternate method, which is reportedly an economically and industrially viable method for production of Bicalutamide, the key feature of which comprises oxidation of sulfide (II) with:
a) Aqueous hydrogen peroxide ($H_2O_2$) in ethyl acetate as solvent and in presence of sodium tungstate or a solvate there of, phenylphosphonic acid and a phase transfer catalyst; or
b) Monoperpthalic acid prepared from pthalic anhydride and hydrogen peroxide.

When aqueous hydrogen peroxide is employed as oxidizing agent, the oxidation reaction requires that it be carried out in the presence of sodium tungstate, phenyl phosphonic acid and phase transfer catalyst with at least up to 20 fold excess of hydrogen peroxide employed. Use of such large excess of hydrogen peroxide makes the process not particularly safe. Furthermore, use of sodium tungstate, its hydrates and its solvates as well as expensive phase transfer catalysts such as tetrabutylammonium bromide, benzyl trimethylammonium chloride, tetrabutylammonium hydroxide and the like make the method specially not economical.

In the case of oxidation using Monoperpthalic acid apart from the hazards associated with its use, low temperatures of between 0 to −30° C. are recommended, thereby increasing the cost of manufacture.

iv). Shintaku, Tetsuya et al in WO2005/037777 disclose an oxidation reaction with per carboxylic acid, which again is associated with the shortcomings mentioned hereinbefore.

From the foregoing, it would be apparent that the reported methods for synthesis of Bicalutamide suffer from one or more of the following limitations, viz.
a) Use of halogenated solvents specially dichloromethane, which is harmful, potentially carcinogenic, expensive and creates a burden in waste treatment;
b) Use of peroxy acids such as m-chloroperbenzoic acid, hydrogen peroxide, trifluoroperacetic acid Monoperpthalic acid as oxidizing agents, which are highly explosive in nature thereby causing safety and environment concerns;
c) Use of cryogenic temperature as low as −50° C. or higher temperatures of about 80° C., which requires energy and thereby increasing the cost of manufacturing;
d) Use of expensive tungsten, vanadium or chromium compounds which are not only expensive but also create problem in waste disposal; and
e) Use of corrosive chemicals like trifluoroacetic anhydride, which calls for extreme precautions not only in handling as well as create problems in waste disposal.

Further, the by-products of such oxidation reactions e.g. benzoic acid obtained on oxidation when m-chloroperbenzoic acid are also in many instances difficult to remove calling for tedious separation and purification techniques.

Considering the therapeutic and commercial importance of Bicalutamide there exists a need for a method which is free of the limitations of the prior art methods and which, more over is safe, simple convenient and economical.

The present invention is a step forward in this direction and provides a simple convenient and economical method for manufacture of Bicalutamide, which is both industrially and environmentally safe.

OBJECTS OF THE INVENTION

An object of the present invention is to provide a method for preparation of Bicalutamide, which avoids use of peroxy acids.

Another object of the present invention is to provide a method for preparation of Bicalutamide, which avoids use of halogenated solvents.

Yet another object of the present invention is to provide a method for preparation of Bicalutamide, which does not require cryogenic or high temperatures.

Further object of the present invention is to provide a method for preparation of Bicalutamide, which avoids use of expensive tungsten, vanadium and chromium compounds as well as expensive phase transfer catalysts.

Yet further object of the present invention is to provide a method for preparation of Bicalutamide, which avoids use of corrosive chemicals.

Another object process for preparation of Bicalutamide, which is safe, simple, convenient and economical.

From the prior art, reporting various methods utilized for preparation of Bicalutamide it is quite evident all methods invariably utilize a peroxy acid

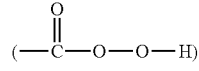

for oxidation of the sulfide (II) compound to give Bicalutamide.

Further, from the teachings of U.S. Pat. No. 4,636,505, it is again evident that only use of a peroxy acid as an oxidizing agent can lead to the formation of a sulfonyl compound i.e., Bicalutamide, whereas use of other oxidizing agents like sodium metaperiodate would result in the formation of a sulfinyl compound i.e., a sulfoxide and not sulfone.

Against this background, the present inventors have found that the sulfide compound (II) can be oxidized completely to the corresponding sulfone (O=S=O) derivative i.e., Bicalutamide (I) using a "Non peroxy acid" agent, which apart from being free of the shortcomings associated in general with use of a peroxy acid or similar agents provides the desired end product i.e., Bicalutamide not only in good yields, but also of quality conforming to pharmacopeial specifications world over.

In particular, the present inventors have found that the sulfide compound (II) can be oxidized to Bicalutamide (I) using potassium permanganate ($KMnO_4$) which:

i) Unlike many of the peroxy acid compounds is highly stable at room temperature;

ii) Unlike many of the peroxy acid compounds is non-hygroscopic and not sensitive to air and moisture;

iii) Unlike many of the peroxy acid compounds is not explosive in nature and therefore easy and safe to handle on an industrial scale;

iv) Unlike many of the peroxy acid compounds is inexpensive and readily available;

v) Forms manganese dioxide ($MnO_2$) as by-product, which can not only be easily removed but also recycled back to potassium permanganate ($KMnO_4$);

vi) The oxidation can be carried out under neutral conditions unlike acidic or basic conditions required for oxidation using a peroxy acid;

vii) Can be carried out in water or a mixture of water and a water miscible environmentally benign solvent, which unlike halogenated solvents are non-carcinogenic, safe and do not cause concern in waste disposal; and Can be carried out at ambient temperatures and does not require cryogenic or very high temperatures.

SUMMARY OF THE INVENTION

Thus the present invention relates to a process for preparation of Bicalutamide of formula (I),

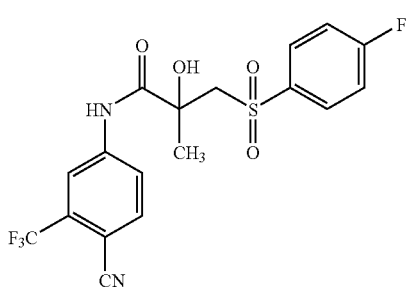

comprising oxidation of compound of formula (II),

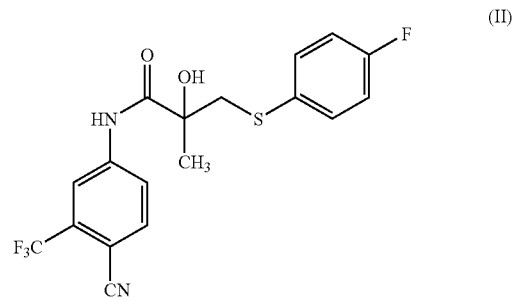

with potassium permanganate in presence of water or a mixture of water and water miscible solvent and isolating Bicalutamide of formula (I) thereof.

The present invention also relates to Bicalutamide prepared by the aforesaid process which exhibits
i) X-ray diffraction pattern as given in FIG. 1.
ii) DSC thermogram as given in FIG. 2.
iii) IR spectrum as given in FIG. 3.
iv) solid state $^{13}C$ NMR spectrum as given in FIG. 4.
X-ray diffraction pattern as given in FIG. 1.

BRIEF DESCRIPTION OF ACCOMPANYING DRAWINGS

DETAILED DESCRIPTION OF THE INVENTION

Figure 1:
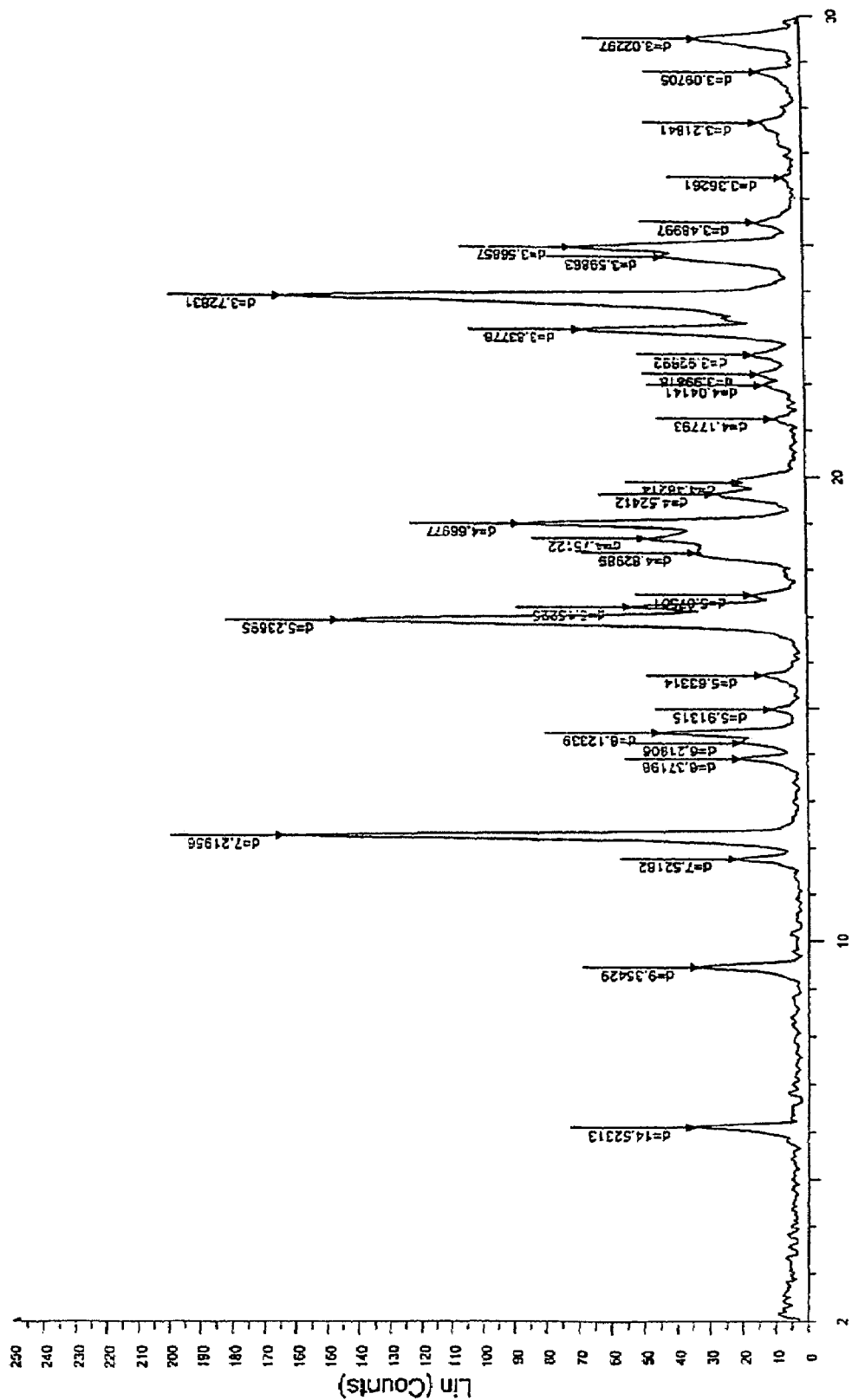
FIG. 1 represents a characteristic X-ray diffraction pattern of Bicalutamide obtained by the method of the present invention.
Figure 2:
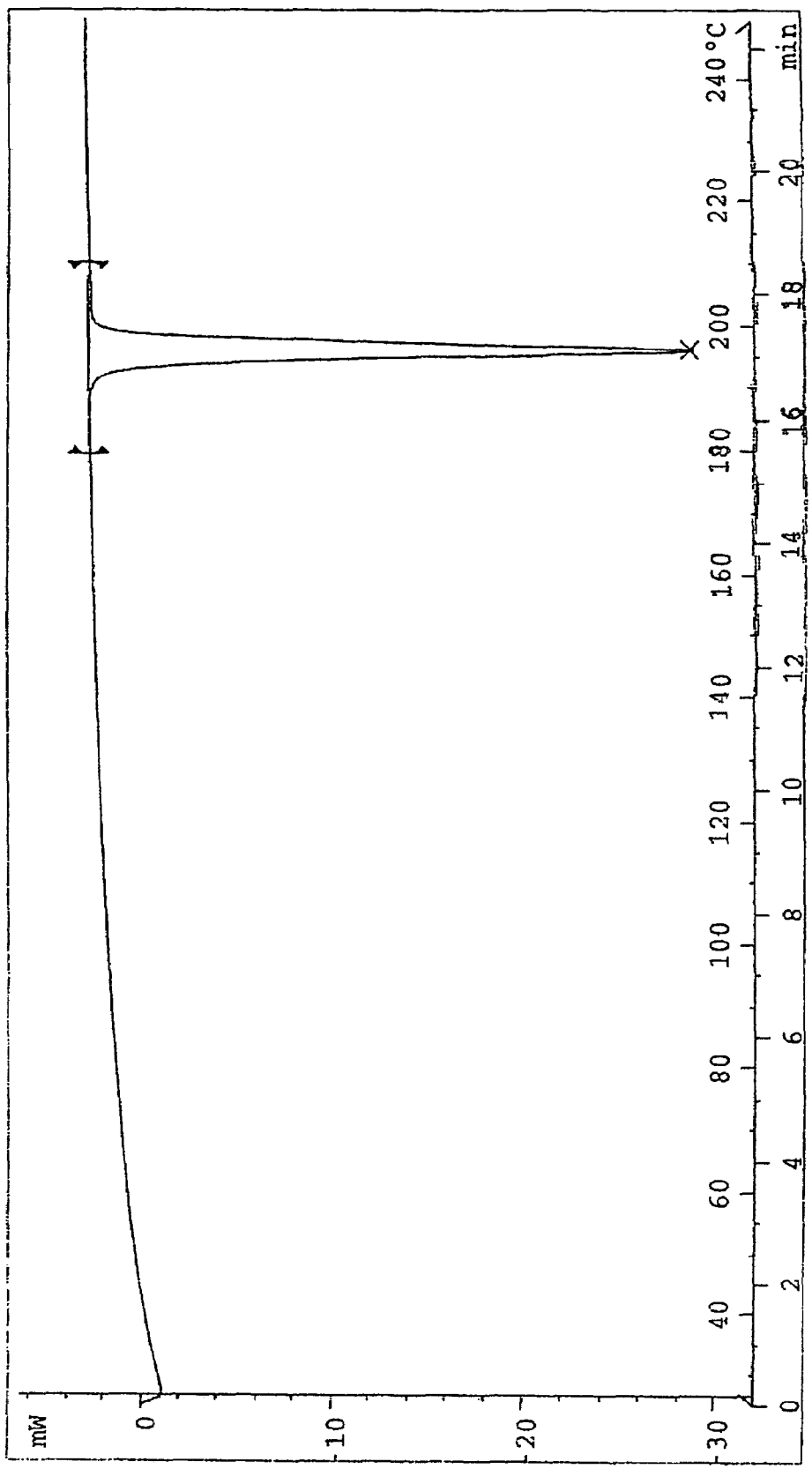
FIG. 2 represents a characteristic DSC thermogram of Bicalutamide obtained by the method of the present invention.
Figure 3:
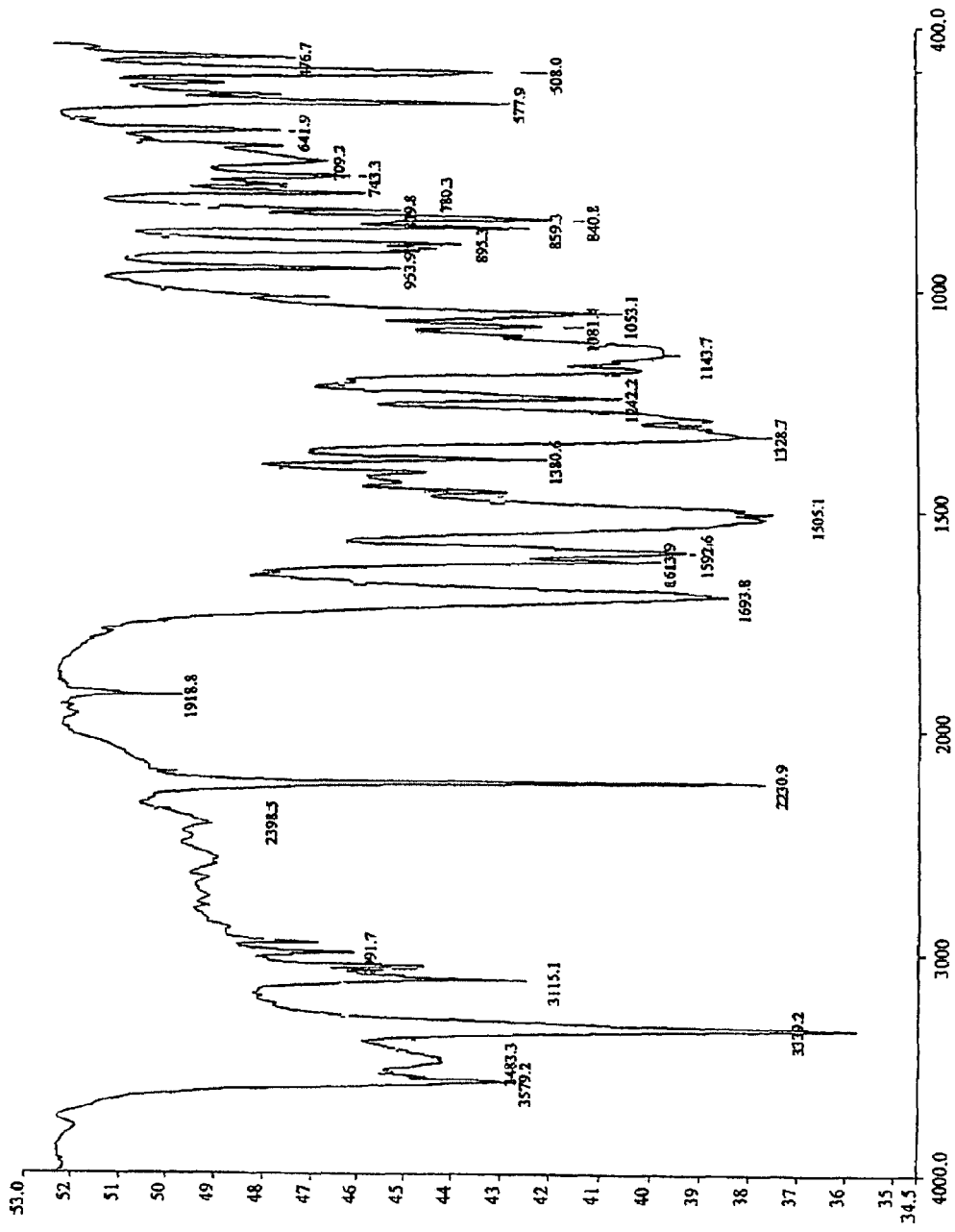
FIG. 3 represents a characteristic IR spectrum of Bicalutamide obtained by the method of the present invention.
Figure 4:
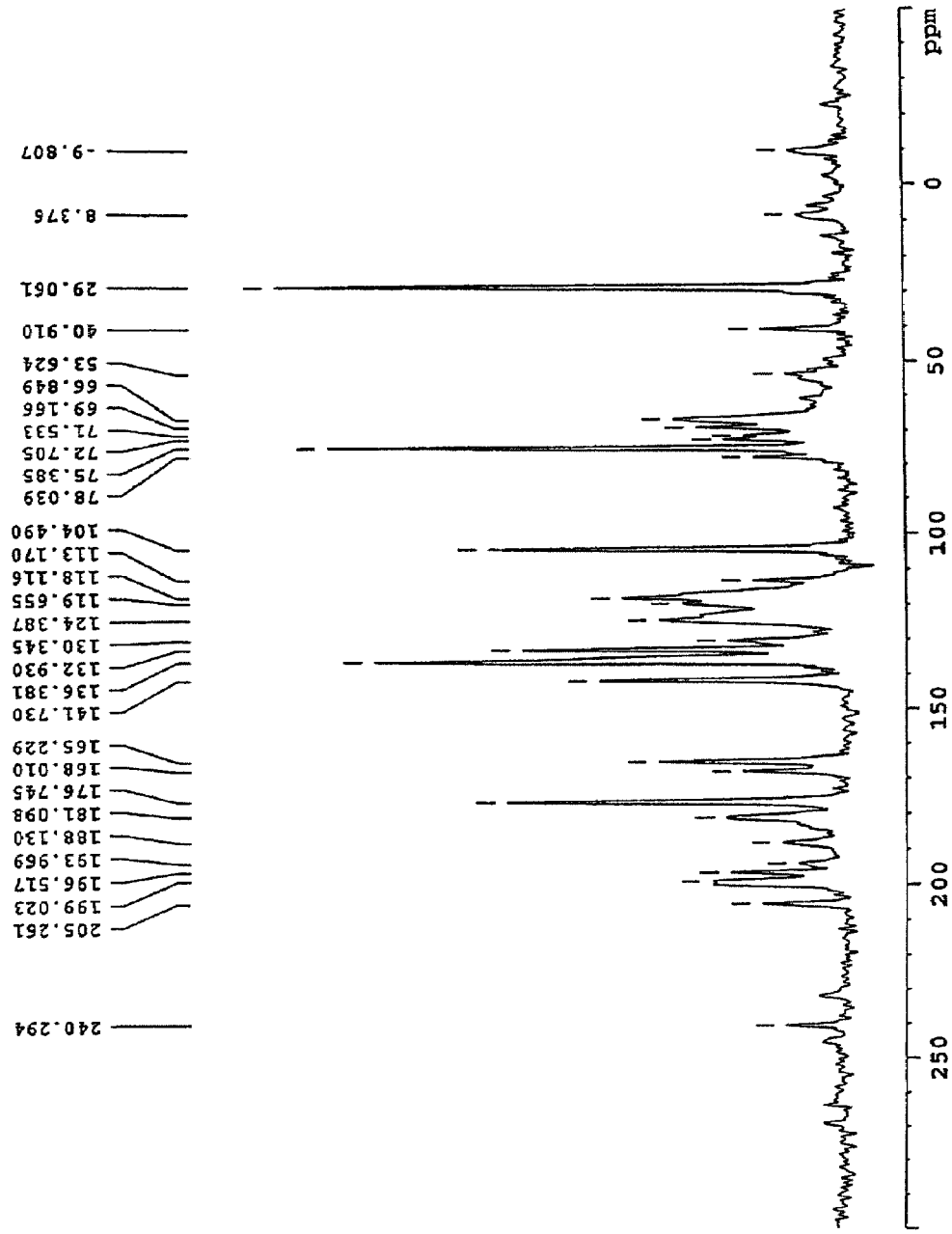
FIG. 4 represents a characteristic solid-state $^{13}C$ NMR spectrum of Bicalutamide obtained by the method of the present invention.

The process of the present invention is further detailed as hereunder.

As mentioned hereinearlier, the oxidation of the sulfide compound of formula (II) is carried out using potassium permanganate in presence of water or water miscible organic solvents such as nitrites, ketones, aliphatic acids etc in admixture with water at ambient temperature or under slight warming.

The oxidation of sulfide (II) compound can be carried out with potassium permanganate:
a) under near neutral conditions;
b) using equivmolar to slight molar excess of potassium permanganate; and In presence of water or a mixture of water and a water miscible environmentally benign solvent selected form nitrites, ketones, aliphatic acids etc in admixture with water, which are not only safe in handling, environmentally benign and do not pose any problem in health and waste disposal.

Potassium permanganate can be employed in equimolar to molar excess of up to three molar equivalents to the sulfide compound (II). Preferably potassium permanganate is employed in the range 2 to 3 molar equivalents per mole of sulfide compound (II).

Water miscible organic solvents that can be employed include nitrites selected from acetonitrile, propionitrile and benzonitrile; ketones such as acetone, methyl isobutyl ketone, methyl ethyl ketone, and cyclohexanone; and aliphatic acids such as acetic acid, propionic acid, and butyric acid.

Amongst nitrites, acetonitrile is more preferred; amongst ketones, acetone is more preferred; and amongst aliphatic acids, acetic acid is more preferred.

Amongst the water miscible solvents, nitrites are more preferred and the most preferred solvent is acetonitrile.

Typically the water or mixture of water and the water miscible organic solvent employed as solvent or reaction medium is 5 to 30 times by volume of the sulfide compound (II) and preferably they are employed in the range of 10 to 15 times by volume of the sulfide compound (II).

The ratio of the water miscible organic organic solvent and water employed can be in a ratio of between 1:1 and 1:4 and preferably the ratio is of between 1:1 and 1:2.

The temperature employed can be between ambient to slightly higher than ambient and is in the range of between 25-60° C. Preferably the temperature employed is in the range of between 25-45° C.

In a typical embodiment, to a solution of the sulfide compound (II) in water or mixture of water and the water miscible organic solvent, kept at a temperature of between 25-35° C. is added potassium permanganate in lots over a period of 30-60 minutes, followed by agitation of the reaction mixture at a temperature of 35-60° C. till completion of the reaction (5-8 hours).

At the end of the reaction, an aqueous solution of sodium bisulfite is added to the reaction mixture and the precipitated solids filtered and washed with water till all permanganate is washed away as indicated by the colourlessness of the filtrate.

The advantage of the method is that at the end of the oxidation the oxidized product i.e., Bicalutamide is generally thrown out from the reaction mixture and can be collected by filtration. Furthermore, the product isolated is generally of very high purity and most importantly is relatively free of manganese dioxide. The product is further crystallized from acetonitrile and, if required can be further purified to match any specific pharmacopoeial requirement through simple techniques.

The solid residue thus obtained is further dissolved in acetonitrile, optionally charcoalised, and filtered through micron filters etc and from which Bicalutamide is crystallized in highly pure form.

Alternatively, the reaction mixture after treatment with sodium bisulfite can be extracted with a water immiscible organic solvent such as ethyl acetate, dichloromethane, dichloroethane etc. The organic layer that contains Bicalutamide is evaporated and the residue is crystallized from acetonitrile as mentioned hereinabove.

The product i.e., Bicalutamide obtained has X-ray diffraction pattern, DSC thermo gram, IR spectrum and solid-state $^{13}C$ NMR spectrum as depicted in FIGS. (1), (2), (3) and (4) respectively.

Alternatively the product can be further crystallized from a mixture of ethyl acetate and petroleum ether as per method disclosed in *Journal of Medicinal Chemistry*, 1988, Vol. 31, No. 5 page 954-959. The product thus obtained is also found to exhibit X-ray diffraction pattern, DSC thermogram, IR spectrum and solid state $^{13}C$ NMR spectrum as depicted in FIGS. (1), (2), (3) and (4) respectively.

The present inventors have carried out oxidation of the sulfide compound (II) using various prior art methods e.g. using hydrogen peroxide and trifluoroacetic anhydride as per the method disclosed in WO 02/24638 A1; using m-chloroperbenzoic acid as per the method disclosed in WO 2004/074350 A2; using peracetic acid as per the method disclosed in WO 02/24638 A1; and using monoperpthalic acid as per the method disclosed in U.S. Pat. No. 6,740,770. The yield of Bicalutamide (41-67%) in all such methods was found to be lower than the yield of Bicalutamide (74%) obtained through oxidation with potassium permanganate as per method of present invention. A comparison of the yield of Bicalutamide obtained by the method of the present invention with that obtained utilizing prior art methods is summarized in Table-1 Bicalutamide obtained by the process of the present invention is found to exhibit an X-ray diffraction pattern, DSC thermogram, IR spectrum and solid state $^{13}C$ NMR spectrum as depicted in FIGS. (1), (2), (3) and (4) respectively.

Alternatively, the Bicalutamide prepared by the present invention can be converted to the known polymorphic forms reported e.g. Form-I and Form-II as disclosed in US 2004/0063782 A1 through utilization of the methods disclosed therein.

TABLE 1

Comparison of yields of Bicalutamide (I) obtained by the method of the present invention vs. that obtained through utilization of prior art methods.

| Sr. No. | Oxidizing Agent | Yield (%) |
| --- | --- | --- |
| 1. | H$_2$O$_2$ & Trifluoroacetic anhydride (WO 02/24638 A1) | 67 |
| 2. | m-CPBA (WO 2004/074350 A2) | 41 |
| 3. | PeraceticAcid. (WO 0224638) | 41 |
| 4. | Monoperpthalic acid (US 2004013303-A1) | 58 |
| 5. | Potassium Permanganate (Method of the Present Invention) | 74 |

The present invention is further illustrated by the following examples, which should not be construed as limiting the scope of the invention.

EXAMPLE 1

To a mixture of acetonitrile (150 ml) and water (100 ml) was added N-[4-cyano-3-(trifluoromethyl) phenyl]-3-[(4-fluorophenyl) thio]-2-hydroxy-2-methyl propanamide [II, 10.0 gm, 0.025 mol] at 25-30° C. The temperature of reaction mixture was raised to 40-45° C. and to the solution was added potassium permanganate (7.94 gm, 0.050 mol, 2.0 eq) in lots over a period of 30 minutes maintaining the temperature between 40-45° C. during addition. The reaction mixture was agitated at 40-45° C. for further time till the completion of reaction. The reaction mixture was cooled to 25-35° C., and to which was added a solution of sodium bisulfite (12 gm) in water (600 ml). The reaction mixture was agitated at 25-35° C. for 6-7 hours and the solid precipitated was filtered and washed with water till the filtrate became colorless.

The solid was dried and dissolved in acetonitrile (50 ml) under heating. To the hot solution was added activated charcoal and the mixture heated to reflux for 1-2 hours. The hot mixture was filtered to remove charcoal and optionally passed through fine microfilters. The filtrate was concentrated, cooled to 25-35° C. and the precipitated solid filtered and dried to give (6.0 gm, 55%) of Bicalutamide having a purity 99.07% and exhibiting the X-ray diffraction pattern, DSC thermogram, IR spectrum and solid state $^{13}$C NMR spectrum as depicted in FIGS. (1), (2), (3) and (4) respectively.

EXAMPLE 2

To a mixture of acetonitrile (150 ml) and water (100 ml) was added N-[4-cyano-3-(trifluoromethyl) phenyl]-3-[(4-fluorophenyl) thio]-2-hydroxy-2-methyl propanamide [(II), 10.0 gm, 0.025 mol] at 25-30° C. The temperature of reaction mixture was raised to 40-45° C. and to the solution was added potassium permanganate (9.93 gm, 0.062 mol, 2.5 eq) in lots over a period of 30 minutes maintaining the temperature between 40-45° C. during addition. The reaction mixture was agitated at 40-45° C. for further time till the completion of reaction. The reaction mixture was cooled to 25-35° C. and to which was added a solution of sodium bisulfite (14 gm) in water (600 ml). The reaction mixture was agitated at 25-35° C. for 6-7 hours and the solid precipitated was filtered and washed with water till the filtrate becomes colorless.

The solid was dried and dissolved in acetonitrile (50 ml) under heating. To the hot solution was added activated charcoal and the mixture heated to reflux for 1-2 hours. The hot mixture was filtered to remove charcoal and optionally passed through fine microfilters. The filtrate was concentrated, cooled to 25-35° C. and the precipitated solid filtered and dried to give (6.8 gm, 63%) of Bicalutamide having a purity 99.77% exhibiting the X-ray diffraction pattern, DSC thermogram, IR spectrum and solid state $^{13}$C NMR spectrum as depicted in FIGS. (1), (2), (3) and (4) respectively.

EXAMPLE 3

To a mixture of acetonitrile (900 ml) and water (600 ml) was added N-[4-cyano-3-(trifluoromethyl) phenyl]-3-[(4-fluorophenyl) thio]-2-hydroxy-2-methyl propanamide [(II), 60 gm, 0.15 mol] at 25-30° C. The temperature of reaction mixture was raised to 40-45° C. and to the solution was added potassium permanganate (72 gm, 0.45 mol, 3.0 eq) in lots over a period of 30 minutes maintaining the temperature between 40-45° C. during addition. The reaction mixture was agitated at 40-45° C. for further time till the completion of reaction. The reaction mixture was cooled to 25-35° C. and to which was added a solution of sodium bisulfite (100 gm) in water (3600 ml). The reaction mixture was agitated at 25-35° C. for 6-7 hours and the solid precipitated was filtered and washed with water till the filtrate becomes colorless.

The solid was dried and dissolved in acetonitrile (300 ml) under heating. To the hot solution was added activated charcoal and the mixture heated to reflux for 1-2 hours. The hot mixture was filtered to remove charcoal and optionally passed through fine microfilters. The filtrate was concentrated, cooled to 25-35° C. and the precipitated solid filtered and dried to give (45 gm, 70%) of Bicalutamide having a purity 99.68% exhibiting the X-ray diffraction pattern, DSC thermogram, IR spectrum and solid state $^{13}$C NMR spectrum as depicted in FIGS. (1), (2), (3) and (4) respectively.

EXAMPLE 4

To a mixture of acetonitrile (150 ml) and water (100 ml) was added N-[4-cyano-3-(trifluoromethyl) phenyl]-3-[(4-fluorophenyl) thio]-2-hydroxy-2-methyl propanamide [(II), 10.0 gm, 0.025 mol] at 25-30° C. The temperature of reaction mixture was raised to 30-35° C. and to the solution was added potassium permanganate (12 gm, 0.076 mol, 3 eq) in lots over a period of 30 minutes maintaining the temperature between 30-35° C. during addition. The reaction mixture was agitated at 30-35° C. for further time till the completion of reaction. The reaction mixture was cooled to 25-35° C., and to which was added a solution of sodium bisulfite (12 gm) in water (600 ml). The reaction mixture was agitated at 25-35° C. for 6-7 hours and the solid precipitated was filtered and washed with water till the filtrate become colorless.

The solid was dried and dissolved in acetonitrile (50 ml) under heating. To the hot solution was added activated charcoal and the mixture heated to reflux for 1-2 hours. The hot mixture was filtered to remove charcoal and optionally passed through fine microfilters. The filtrate was concentrated, cooled to 25-35° C. and the precipitated solid filtered and dried to give (7.30 gm, 67%) of Bicalutamide having a purity 99.8% exhibiting the X-ray diffraction pattern, DSC thermogram, IR spectrum and solid state $^{13}$C NMR spectrum as depicted in FIGS. (1), (2), (3) and (4) respectively.

EXAMPLE 5

To a mixture of acetonitrile (150 ml) and water (100 ml) was added N-[4-cyano-3-(trifluoromethyl) phenyl]-3-[(4-fluorophenyl) thio]-2-hydroxy-2-methyl propanamide [(II) 10.0 gm 0.025 mol] at 25-30° C. The temperature of reaction mixture was raised to 40-45° C. and to the solution was added potassium permanganate (12 gm, 0.076 mol, 3 eq) in lots over a period of 30 minutes maintaining the temperature between 40-45° C. during addition. The reaction mixture was agitated at 40-45° C. for further time till the completion of reaction. The reaction mixture was cooled to 25-35° C., to which was added a solution of sodium bisulfite (12 gm) in water (600 ml). The reaction mixture was agitated at 25-35° C. for 6-7 hours and the solid precipitated was filtered and washed with water till the filtrate become colorless.

The solid was dried and dissolved in acetonitrile (50 ml) under heating. To the hot solution was added activated charcoal and the mixture heated to reflux for 1-2 hours. The hot mixture was filtered to remove charcoal and optionally passed through fine microfilters. The filtrate was concentrated, cooled to 25-35° C. and the precipitated solid filtered and dried to give (6.0 gm, 55%) of Bicalutamide having a purity 99.07% exhibiting the X-ray diffraction pattern, DSC thermogram, IR spectrum and solid state $^{13}$C NMR spectrum as depicted in FIGS. (1), (2), (3) and (4) respectively.

EXAMPLE 6

To a mixture of acetonitrile (150 ml) and water (100 ml) was added N-[4-cyano-3-(trifluoromethyl) phenyl]-3-[(4-fluorophenyl) thio]-2-hydroxy-2-methyl propanamide [(II) 10.0 gm, 0.025 mol] at 25-30° C. The temperature of reaction mixture was raised to 50-60° C. and to the solution was added potassium permanganate (12 gm, 0.076 mol, 3 eq) in lots over a period of 30 minutes maintaining the temperature between 50-60° C. during addition. The reaction mixture was agitated at 50-60° C. for further time till the completion of reaction. The reaction mixture was cooled to 25-35° C., to which was added a solution of sodium bisulfite (12 gm) in water (600 ml). The reaction mixture was agitated at 25-35° C. for 6-7 hours and the solid precipitated was filtered and washed with water till the filtrate become colorless.

The solid was dried and dissolved in acetonitrile (50 ml) under heating. To the hot solution was added activated charcoal and the mixture heated to reflux for 1-2 hours. The hot mixture was filtered to remove charcoal and optionally passed through fine microfilters. The filtrate was concentrated, cooled to 25-35° C. and the precipitated solid filtered and dried to give (6.0 gm, 55%) of Bicalutamide having a purity 99.07% exhibiting the X-ray diffraction pattern, DSC thermogram, IR spectrum and solid state $^{13}$C NMR spectrum as depicted in FIGS. (1), (2), (3) and (4) respectively.

EXAMPLE 7

To a mixture of acetonitrile (100 ml) and water (100 ml) was added N-[4-cyano-3-(trifluoromethyl) phenyl]-3-[(4-fluorophenyl) thio]-2-hydroxy-2-methyl propanamide [(II) 10.0 gm, 0.025 mol] at 25-30° C. The temperature of reaction mixture was raised to 40-45° C. and to the solution was added potassium permanganate (12 gm, 0.076 mol, 3 eq) in lots over a period of 30 minutes maintaining the temperature between 40-45° C. during addition. The reaction mixture was agitated at 40-45° C. for further time till the completion of reaction. The reaction mixture was cooled to 25-35° C., to which was added a solution of sodium bisulfite (12 gm) in water (600 ml). The reaction mixture was agitated at 25-35° C. for 6-7 hours and the solid precipitated was filtered and washed with water till the filtrate becomes colorless.

The solid was dried and dissolved in acetonitrile (50 ml) under heating. To the hot solution was added activated charcoal and the mixture heated to reflux for 1-2 hours. The hot mixture was filtered to remove charcoal and optionally passed through fine microfilters. The filtrate was concentrated, cooled to 25-35° C. and the precipitated solid filtered and dried to give (6.0 gm, 55%) of Bicalutamide having a purity 99.07% exhibiting the X-ray diffraction pattern, DSC thermogram, IR spectrum and solid state $^{13}$C NMR spectrum as depicted in FIGS. (1), (2), (3) and (4) respectively.

EXAMPLE 8

To a mixture of acetone (150 ml) and water (100 ml) was added N-[4-cyano-3-(trifluoromethyl) phenyl]-3-[(4-fluorophenyl) thio]-2-hydroxy-2-methyl propanamide [(II) 10.0 gm, 0.025 mol] at 25-30° C. The temperature of reaction mixture was raised to 40-45° C. and to the solution was added potassium permanganate (12 gm, 0.076 mol, 3 eq) in lots over a period of 30 minutes maintaining the temperature between 40-45° C. during addition. The reaction mixture was agitated at 40-45° C. for further time till the completion of reaction. The reaction mixture was cooled to 25-35° C. to which was added a solution of sodium bisulfite (24 gm) in water (600 ml). The reaction mixture is agitated at 25-35° C. for 6-7 hours and the solid precipitated was filtered and washed with water till the filtrate become colorless.

The solid was dried and dissolved in acetonitrile (50 ml) under heating. To the hot solution was added activated charcoal and the mixture heated to reflux for 1-2 hours. The hot mixture was filtered to remove charcoal and optionally passed through fine microfilters. The filtrate was concentrated, cooled to 25-35° C. and the precipitated solid filtered and dried to give (4.5 gm, 41.66%) of Bicalutamide having a purity 99.34% exhibiting the X-ray diffraction pattern, DSC thermogram, IR spectrum and solid state $^{13}$C NMR spectrum as depicted in FIGS. (1), (2), (3) and (4) respectively.

EXAMPLE 9

To a mixture of acetonitrile (900 ml) and water (600 ml) was added N-[4-cyano-3-(trifluoromethyl) phenyl]-3-[(4-fluorophenyl) thio]-2-hydroxy-2-methyl propanamide [(II), 60 gm, 0.15 mol] at 25-30° C. The temperature of reaction mixture was raised to 40-45° C. and to the solution was added potassium permanganate (72 gm, 0.45 mol, 3 eq.) in lots over a period of 30 minutes maintaining the temperature between 40-45° C. during addition. The reaction mixture was agitated at 40-45° C. for further time till the completion of reaction. The reaction mixture was cooled to 25-35° C. to which was added a solution of sodium bisulfite (100 gm) in water (3600 ml). The reaction mixture was agitated at 25-35° C. for 6-7 hours and the solid precipitated was filtered and washed with water till the filtrate become colorless.

The solid was dried and dissolved in acetonitrile (300 ml) under heating. To the hot solution was added activated charcoal and the mixture heated to reflux for 1-2 hours. The hot mixture was filtered to remove charcoal and optionally passed through fine microfilters. The filtrate was concentrated, cooled to 25-35° C. and the precipitated solid filtered and dried to give (45 gm, 70%) of Bicalutamide having a purity 99.67% exhibiting the X-ray diffraction pattern, DSC thermogram, IR spectrum and solid state $^{13}$C NMR spectrum as depicted in FIGS. (1), (2), (3) and (4) respectively.

EXAMPLE 10

To water (500 ml) was added N-[4-cyano-3-(trifluoromethyl) phenyl]-3-[(4-fluorophenyl) thio]-2-hydroxy-2-methyl propanamide [(II), 50.0 gm, 0.1256 mol] at 25-30° C. The temperature of reaction mixture was raised to 40-45° C. and to the solution was added potassium permanganate (60 gm, 0.3797 mol, 3 eq) in lots over a period of 30 minutes maintaining the temperature between 40-45° C. during addition. The reaction mixture was agitated at 40-45° C. for further time till the completion of reaction. The reaction mixture was cooled to 25-35° C., to which was added a solution of sodium bisulfite (120 gm) in water (2000 ml). The reaction mixture was agitated at 25-35° C. for 6-7 hours and the solid precipitated was filtered and washed with water till the filtrate become colorless.

The solid was dried and dissolved in acetonitrile (250 ml) under heating. To the hot solution was added activated charcoal and the mixture heated to reflux for 1-2 hours. The hot mixture was filtered to remove charcoal and optionally passed through five microfilters. The filtrate was concentrated, cooled to 25-35° C. and the precipitated solid filtered and dried to give (7.0 gm, 64.8%) of Bicalutamide having a purity 99.4% exhibiting the X-ray diffraction pattern, DSC thermogram, IR spectrum and solid state $^{13}$C NMR spectrum as depicted in FIGS. (1), (2), (3) and (4) respectively.

EXAMPLE 11

To a hot ethyl acetate kept at temperature between 80-90° C. was added Bicalutamide (756.5 gm) obtained by any of the methods described in examples 1-10 to get a clear solution. To the hot solution was added petroleum ether (60-80° C.; 3.4 ltrs), wherein the solution starts becoming turbid. More ethyl acetate (94.5 ltrs) was added to get a clear solution. The solution was cooled to 25-30° C. and further 0-5° C. and maintained at this temperature for 3 hrs. The crystallized solid was filtered and dried at 60-70° C. to give pure Bicalutamide (600 gm) having a purity 99.91% exhibiting the X-ray diffraction pattern, DSC thermogram, IR spectrum and solid state $^{13}$C NMR spectrum as depicted in FIGS. (1), (2), (3) and (4) respectively.

The invention claimed is:

1. A process for preparation of Bicalutamide of formula (I),

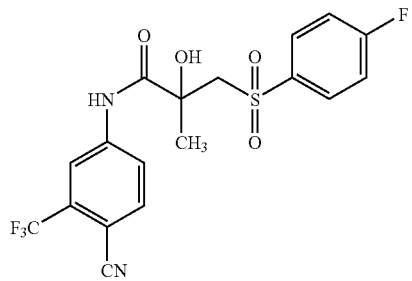

comprising:
oxidizing of compound of formula (II),

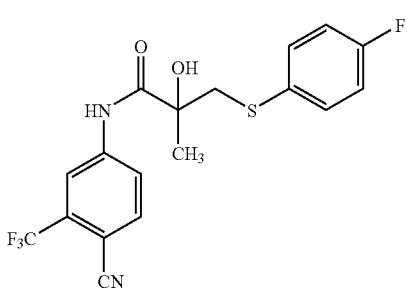

with potassium permanganate in presence of water or with potassium permanganate in the presence of a mixture of water and water miscible solvent; and
isolating Bicalutamide of formula (I).

2. A process according to claim 1, wherein oxidizing is carried out at a temperature of 25-60° C.

3. A process according to claim 1, wherein oxidizing is carried out at a temperature of 25-45° C.

4. A process according to claim 1, wherein the water miscible solvent is selected from a nitrile, a ketone and an aliphatic acid.

5. A process according to claim 4, wherein the nitrile is selected from acetonitrile, propionitrile and benzonitrile.

6. A process according to claim 4, wherein the ketone is selected from acetone, methyl isobutyl ketone, methyl ethyl ketone and cyclohexanone.

7. A process according to claim 4, wherein the aliphatic acid is selected from acetic acid, propionic acid and butyric acid.

8. A process according to claim 1, wherein the water miscible organic solvent comprises acetonitrile.

9. A process according to claim 1, wherein the water miscible organic solvent comprises acetone.

10. A process according to claim 1, wherein the water miscible organic solvent comprises acetic acid.

11. A process according to claim 1, wherein the ratio of water to the water miscible organic solvent is between 1:1 and 1:4.

12. A process according to claim 1, wherein the ratio of water to the water miscible organic solvent is between 1:1 and 1:2.

13. A process according to claim 1, wherein potassium permanganate is in molar proportions of 1 to 3 equivalent per mole of compound of formula (II).

14. A process according to claim 1, wherein potassium permanganate is in molar proportions of 2 to 3 equivalent per mole of compound of formula (II).

15. A process according to claim 1, wherein isolated Bicalutamide of formula (I) employs acetonitrile.

16. A process according to claim 15, further comprising crystallizing Bicalutamide of formula (I) from a mixture of ethyl acetate and petroleum ether.

17. A process for preparation of Bicalutamide of formula (I)

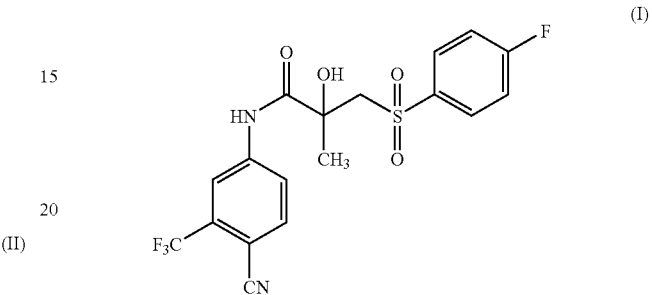

comprising:
oxidizing a compound of formula (II),

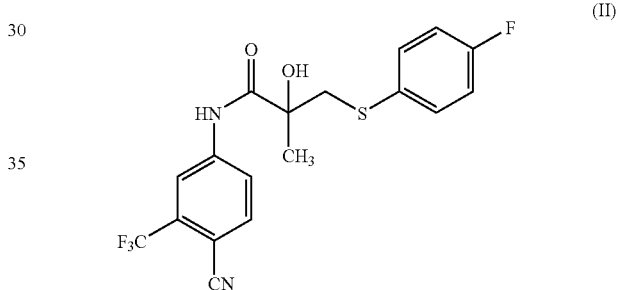

with potassium permanganate in the presence of water or with potassium permanganate in the presence of a mixture of water and water miscible solvent; wherein the water miscible solvent comprises acetonitrile, propionitrile, benzonitrile, acetone, methyl isobutyl ketone, methyl ethyl ketone, cyclohexanone, acetic acid, propionic acid, or butyric acid; and
isolating Bicalutamide of formula (I).

18. The process of claim 17, wherein the water miscible organic solvent comprises acetonitrile, acetone, or acetic acid.

19. The process of claim 18, wherein the water miscible organic solvent comprises acetonitrile.

20. The process of claim 17, wherein the ratio of water to the water miscible organic solvent is 1:1 to 1:4.

21. The process of claim 17, wherein potassium permanganate is in molar proportions of 1 to 3 equivalent per mole of compound of formula (II).

22. The process of claim 17, wherein isolating employs acetonitrile.

23. The process of claim 22, further comprising crystallizing Bicalutamide of formula (I) from a mixture of ethyl acetate and petroleum ether.

* * * * *